US008641983B2

(12) United States Patent
Noto (10) Patent No.: US 8,641,983 B2
(45) Date of Patent: Feb. 4, 2014

(54) CLEANING APPARATUS FOR SANITIZING FURNISHINGS

(76) Inventor: Anthony Peter Noto, Knightdale, NC (US)

( * ) Notice: Subject to any disclaimer, the term of this patent is extended or adjusted under 35 U.S.C. 154(b) by 541 days.

(21) Appl. No.: 12/909,276

(22) Filed: Oct. 21, 2010

(65) Prior Publication Data

US 2011/0095206 A1    Apr. 28, 2011

Related U.S. Application Data (60) Provisional application No. 61/254,183, filed on Oct. 22, 2009, provisional application No. 61/254,193, filed on Oct. 22, 2009.

(51) Int. Cl.
*A61L 2/00*    (2006.01)

(52) U.S. Cl.
USPC .......................................................... 422/300

(58) Field of Classification Search
USPC ........................................ 422/300; 250/492.1
See application file for complete search history.

(56) References Cited

U.S. PATENT DOCUMENTS

| 4,809,384 | A  | * | 3/1989 | Yokota et al. .................. 15/103 |
| 2006/0048800 | A1 | * | 3/2006 | Rast et al. .................. 134/56 R |
| 2008/0011440 | A1 | * | 1/2008 | Rajanummi et al. ........... 162/272 |
| 2010/0112677 | A1 | * | 5/2010 | Onishi et al. ............... 435/283.1 |
| 2010/0127189 | A1 | * | 5/2010 | Boyarsky et al. ........... 250/492.2 |

* cited by examiner

Primary Examiner — Kevin Joyner
(74) Attorney, Agent, or Firm — NK Patent Law, PLLC (57) ABSTRACT A cleaning apparatus is provided. The apparatus includes a mount member configured for extending along a dimension of an article to be cleaned and maintaining a predetermined distance from an apparatus facing surface of the article to be cleaned. A first engaging member is carried on a first end of the mount member and a second engaging member carried on a second end of the mount member. The first and second engaging members cooperate for engagement about the article to be cleaned. A casing is carried by the mount member and is configured for slideable translation about the mount member along the dimension of the article. The casing also defines an article sanitizing portion on an article facing portion thereof. The article sanitizing portion includes at least one sanitizing device for sanitizing the article to be cleaned.

22 Claims, 10 Drawing Sheets

CLEANING APPARATUS FOR SANITIZING FURNISHINGS

CROSS REFERENCE TO RELATED APPLICATIONS

This application claims priority to U.S. Provisional Patent Application No. 61/254,183 filed on Oct. 22, 2009, and 61/254,193 filed on Oct. 22, 2009, the contents of both of which are hereby incorporated by reference.

TECHNICAL FIELD

The presently disclosed subject matter is directed towards a cleaning apparatus for sanitizing an article to be cleaned, and more particularly, towards a cleaning apparatus for sanitizing room furnishings such as bedding furniture using a sanitization device such as ultraviolet light.

BACKGROUND

In order to clean furnishings in places such as a private residence, hotel, or hospital, the covering articles are removed from the furnishings and are typically washed in a washing machine. This may be an effective manner in cleaning the covering articles, however, this does not effectively clean the underlying furnishings that those articles cover such a bed or pillow. The underlying furnishings are susceptible to bacteria, virus, mold, fungi, dust mites, fleas, lice, bed bugs, dead human skin, and other unwanted and potentially unsafe toxins, organisms, and human by-products.

The underlying furnishings are difficult to clean for several reasons. One such reason is that the underlying furnishings are not easily portable to transport to a washing machine. The underlying furnishings may be bulky or heavy. Additionally, the unwanted and potentially unsafe toxins, organisms, and human by-products that may be found in underlying furnishings are not always effectively cleaned by traditional cleaning methods known in the art. For example, the bedding articles such as sheets or covers can be simply cleaned by soaking in a soap detergent solution. However, the underlying articles cannot be easily cleaned in this manner because they are difficult to dry due to increased mass, water retention, and surface area. The underlying articles could be vacuumed; however, this is a manual process and does not sanitize many of the microorganisms, toxins, and human by-products.

Devices incorporating ultraviolet light or steam have been developed to clean underlying furnishings. These devices are generally hand-held devices that must be manually scanned over the underlying furnishing. These devices suffer from a variety of disadvantages including that they are hand operated, are small in size and thus take substantial time to use, may expose the operator to ultraviolet light, don't effectively clean some microorganisms, toxins, and human by-products, and don't collect any of the dead matter or debris.

Accordingly, a need exists for a manner to clean underlying furnishings that addresses the various disadvantages associated with the prior art.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

Disclosed herein is a cleaning apparatus. The cleaning apparatus includes a mount member configured for extending along a major dimension of an article to be cleaned. A first engaging member is carried on a first end of the mount member and a second engaging member is carried on a second end of the mount member. The first and second engaging members cooperate for engagement about the article to be cleaned. A casing is configured for slideable translation about the mount member along the major dimension of the article to be cleaned and defines a volume in which a sanitizing device is carried therein.

According to another aspect, the apparatus also includes a drive motor coupled to the casing for translating the casing about the mount member.

According to another aspect, the casing carries a collar that is slideably received on the mount member.

According to another aspect, the sanitizing device comprises an ultraviolet light source for sanitizing the article to be cleaned.

According to another aspect, the sanitizing device comprises a vacuum for sanitizing the article to be cleaned.

According to another aspect, the sanitizing device includes a fluid spraying device for spraying fluids for sanitizing the article to be cleaned.

According to another aspect, the casing further carries a perturbator for perturbing the article to be cleaned.

According to another aspect, the first and second engaging members each define a horizontally extending stop member for resting upon an apparatus facing surface of the article to be cleaned. The horizontally extending stop members are selectively positionable about each respective first and second engaging members to thereby adjust a distance between an article facing surface of the casing and an apparatus facing surface of the article to be cleaned.

According to another aspect, the mount member is extendable to fit the article to be cleaned.

According to another aspect, the casing defines end sections that are hingedly coupled to a main section.

According to another aspect, a cleaning apparatus is provided. The apparatus includes a mount member configured for extending along a major dimension of an article to be cleaned and maintaining a predetermined distance from an apparatus facing surface of the article to be cleaned. A casing is carried by the mount member and is configured for slideable translation about the mount member along the major dimension of the article. The casing also defines an article sanitizing portion on an article facing portion thereof. The article sanitizing portion includes a sanitizing device for sanitizing the article to be cleaned.

According to another aspect, the sanitizing device consists of an ultraviolet light source for sanitizing the article to be cleaned, a vacuum for sanitizing the article to be cleaned, a fluid dispensing device for spraying fluids for sanitizing the article to be cleaned, or a combination thereof.

According to another aspect, a cleaning apparatus is provided. The apparatus includes a mount member configured for extending along a major dimension of an article to be cleaned and maintaining a predetermined distance from an apparatus facing surface of the article to be cleaned. A first engaging member is carried on a first end of the mount member and a second engaging member is carried on a second end of the mount member. The first and second engaging members cooperate for engagement about the article to be cleaned. A casing is carried by the mount member and is configured for slideable translation about the mount member along the major dimension of the article. The casing also defines an article sanitizing portion on an article facing portion thereof.

The article sanitizing portion includes a sanitizing device for sanitizing the article to be cleaned.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings.

DETAILED DESCRIPTION

The presently disclosed invention is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
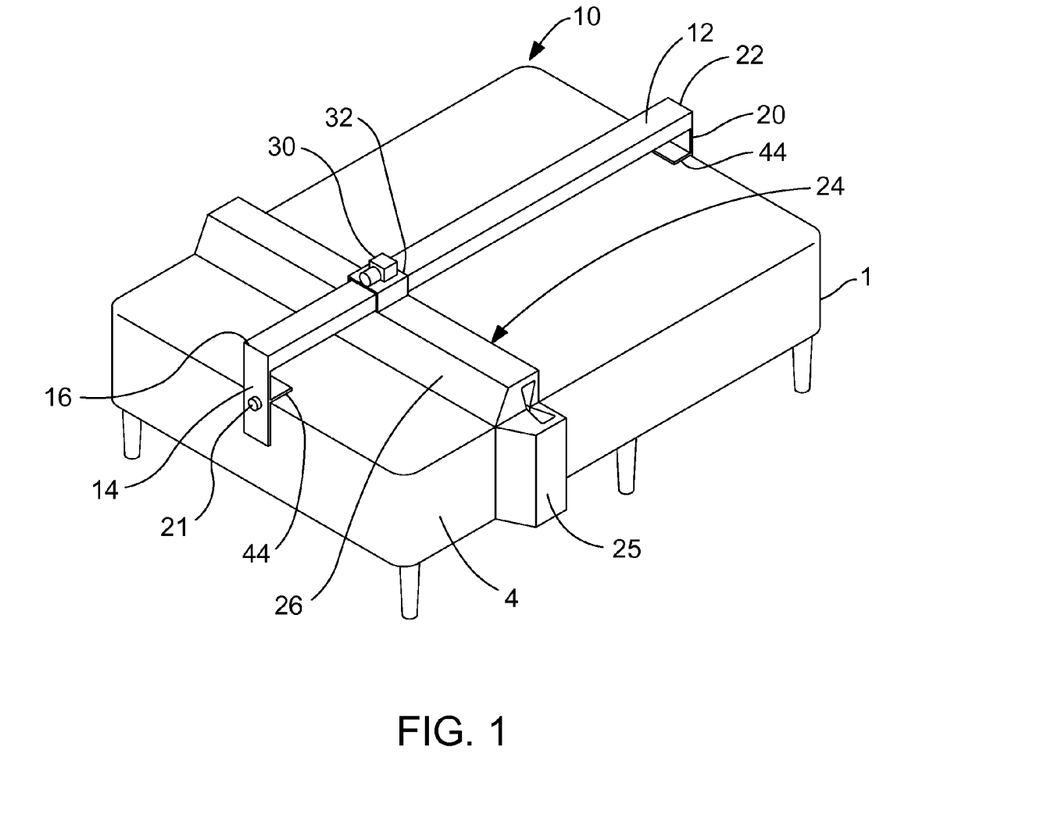
FIG. 1 is a perspective view of a cleaning apparatus installed upon an article to be cleaned.

FIG. 1 is a cleaning apparatus for use with sanitizing articles to be cleaned and is generally designated as 10 throughout the Figures. The apparatus 10 includes a mount member 12 that may be configured for extending along a major dimension of an article to be cleaned 1, such as a bed depicted in FIG. 1. The mount member 12 may be adjustable in length by any variety of known mechanisms in the prior art, including telescopic adjustment such that the length of the mount member 12 may be adjusted to fit articles 1 of varying dimensions. The mount member 12 may include a first engaging member 14 carried on a first end 16 of the mount member 12 and a second engaging member 20 carried on a second end 22 of the mount member 12. The first engaging member 14 and the second engaging member 20 cooperate for engagement about the article to be cleaned 1 by forming an engagement fit about opposing surfaces that are defined at the end of the major dimension of the article 1.

As illustrated in FIGS. 1, 2A, 2B, 3, and 4, the apparatus 10 is engageable about the article to be cleaned 1, which is illustrated as a bed throughout the Figures. A pair of horizontally extending stop members 44 may be provided for engaging an apparatus facing surface 3 of the article to be cleaned 1 and may be provided for engagement with an article such as the bed shown in the Figures. Each of the horizontally extending stop members 44 may be provided with adjustability to alter their placement along each of the first engaging member 14 and the second engaging member 20 to thereby adjust the relative positioning of the apparatus 10 about the article to be cleaned 1. For example, each of the first engaging member 14 and the second engaging member 20 may define a plurality of apertures therein that, in combination with a threaded recess defined in the horizontally extending stop members 44, cooperatively receive a threaded knob assembly 21 to thereby provide adjustability of the position of the stop members 44. However, any article, including, but not limited to rugs, carpets, bed spreads, bed linens, pillows, underside of beds, couches, and other furnishings may be sanitized by apparatus 10.

The apparatus 10 includes a casing 24 that is configured for slideable translation about the mount member 12 along the article to be cleaned 1. The casing 24 generally defines a volume in which a sanitizing device is carried therein. The casing 24 may carry a collar 32 that is configured for slideably receiving the mount member 12. A drive motor 30 is coupled to the casing 24 for translating the casing 24 about the mount member 12. This may be accomplished by a geared assembly or any other suitable mechanism. The drive motor 30 may be powered by an internal energy storage device such as a battery or may be coupled to an electrical cord for coupling with an electrical outlet. The casing 24 is also configured such that the drive motor 30 may not be required, and the casing 24 may be translated by pushing and pulling thereon by the operator. The casing 24 further defines end sections 25 that are hingedly coupled to a main section 26 for sanitizing outwardly facing surfaces 4 of the article to be cleaned 1. In one or more embodiments, the casing 24 may be provided with guide wheels or the like on an article facing surface thereof for maintaining contact with the article to be cleaned 1.

Figure 2A:
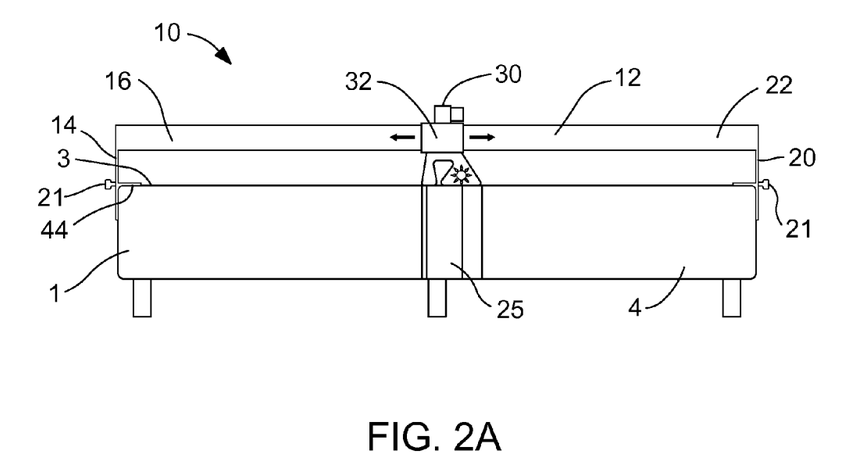
FIG. 2A is a side view of a cleaning apparatus installed upon an article to be cleaned.
Figure 2B:
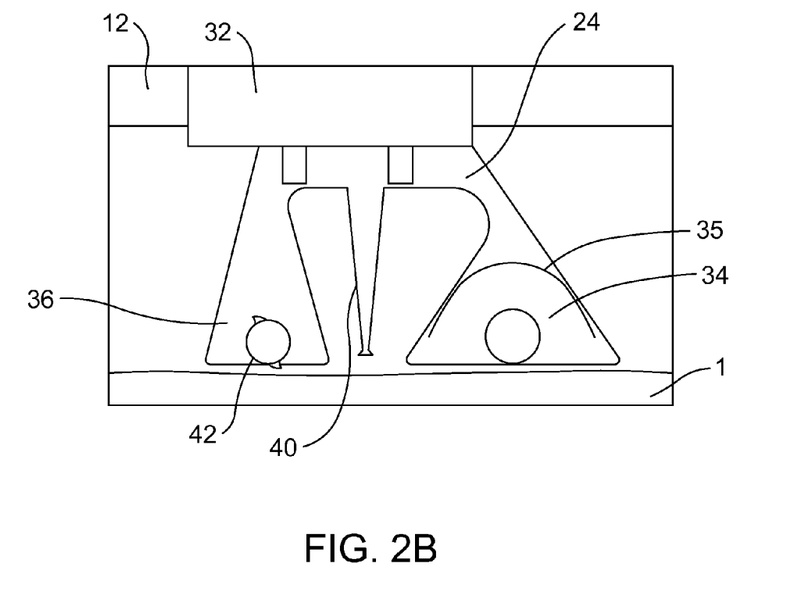
FIG. 2B is a enlarged, cross-sectional view of a sanitizing device carried by the cleaning apparatus depicted in FIG. 2A.
Figure 3:
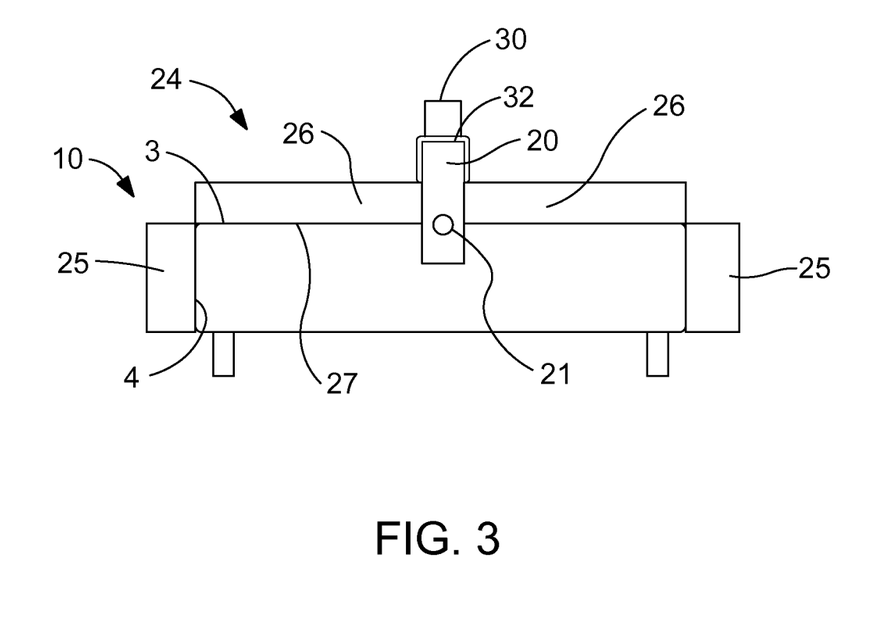
FIG. 3 is a front view of a cleaning apparatus installed upon an article to be cleaned.
Figure 4:
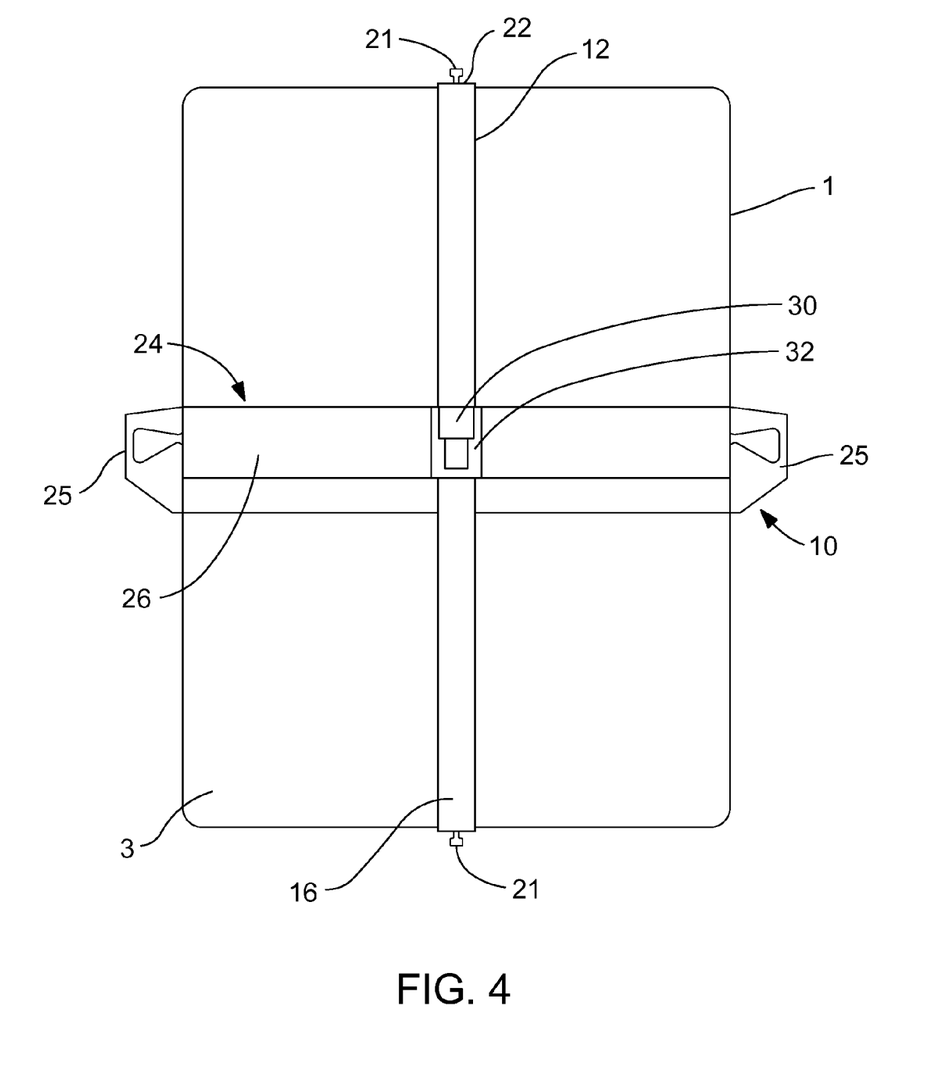
FIG. 4 is a top view of a cleaning apparatus installed upon an article to be cleaned.
Figure 5:
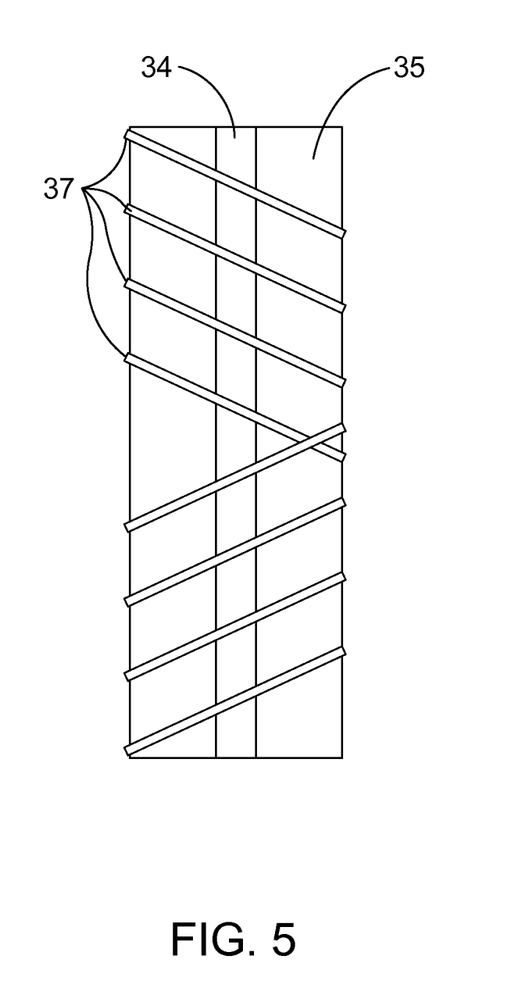
FIG. 5 is a bottom view of a sanitizing device for use with the cleaning apparatus, and more particularly, an ultraviolet light for sanitizing the article to be cleaned.

As illustrated in FIG. 2B, the casing 24 is configured for carrying various sanitizing devices. For example, a light 34 may be provided for sanitizing microorganisms that can be eliminated by a light source. The light 34 may be any appropriate light source, and in one or more embodiments, may be an ultraviolet light such as UV-C. As illustrated in FIGS. 2B and 5, a parabolic reflector 35 may be provided about the light 34 for increasing the concentration of light directed at the article to be cleaned 1. A plurality of guide bars 37 may be provided about the light for maintaining the article to be cleaned 1 away from direct contact with the light 34. The guide bars 37 are arranged in generally spaced-apart arrangement and at an angle relative to the light 34 such that at some point during the scanning process, the light 34 will not be obstructed by the guide bars 37. In one or more alternate embodiments, a light transmissive panel may be used in lieu of the guide bars 37, and may be a TEFLON® panel.

A vacuum 36 for sanitizing the article to be cleaned 1 may also be provided. The vacuum 36 may have an internal vacuum pump carried within the casing 24 or may have an external vacuum pump that is sealably attached to the vacuum 36. Likewise, a vacuum tank may be carried within the casing 24 or may be provided at an external location for storing vacuumed substances. The vacuum 36 is particularly advantageous because the vacuum 36 may vacuum away those microorganisms and toxins that the light 34 eradicates as well as human by-products embedded within the article to be cleaned 1. The casing 24 may also include a perturbator 42 for providing mechanical agitation to the article to be cleaned 1. The perturbator 42 may also be coupled to a rake or comb apparatus for separating fibers of the article to be cleaned 1 for increased penetration of the light 34.

A fluid dispenser 40 may also be provided within the casing 24. The fluid dispenser 40 may be provided for spraying steam, ozone, liquid, gas or other chemicals for sanitizing or providing aromas to the article to be cleaned 1. In other embodiments, multiple dispensers may be provided for spraying various chemicals or fluids.

In operation, if necessary, the relative positioning of the casing 24 is adjusted to a predetermined height or distance away from the article to be cleaned 1 by selection of the appropriately placed aperture and threaded recess on the first and second engaging members 14, 20 and the horizontally extending stop members 44, respectively, and then insertion of the threaded knob assembly 21.

Figure 6:
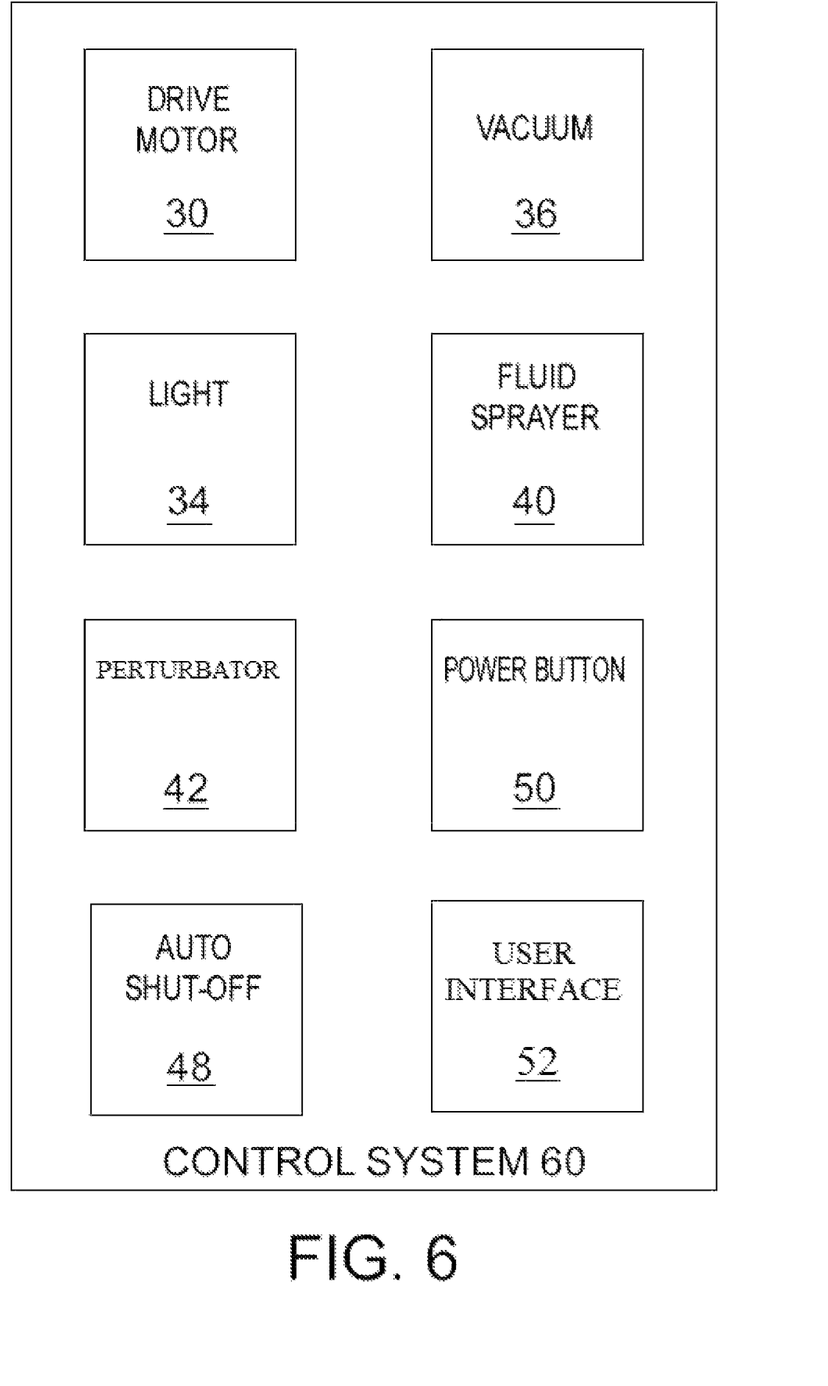
FIG. 6 is a schematic view of a control system for use with the cleaning apparatus.

The apparatus 10 includes a control system for providing control signals thereto. For example, as illustrated in FIG. 6, the control system 60 may be in communication with the light 34, vacuum 36, fluid spraying device 40, perturburator 42 that may also include a brush, drive motor 30, an auto-shut off feature 48, a power switch 50 for powering on and off the apparatus 10, and a user interface 52. The vacuum pressure may be controlled or cycled to prevent collecting the item being cleaned. The auto-shut off feature 48 may be provided for detecting when the apparatus 10 has reached an end of the article to be cleaned 1 or has been in operation for a predetermined period of time. In this manner, once the apparatus 10 has reached an end of the article to be cleaned 1 or has been in operation for a predetermined period of time, the auto-shut off feature 48 may power off the apparatus 10, display a visual or audible indication of completion, or any combination thereof. The control system 60 may also be in communication with at least one safety switch to prevent accidental exposure to ultraviolet light or fluid spray from the light 34 and fluid spraying device 40, respectively.

The user interface 52 is provided for allowing the operator to select operating conditions for the apparatus 10. For example, the operator may desire that only the light 34 and vacuum 36 operation be conducted on the article to be cleaned 1. The user interface allows the operator to select these desired operations and communicates those instructions to the control system 60. In another example, the operator may desire a longer cleaning cycle and select such a longer cleaning cycle on the user interface 52 for communicating with the control system 60.

Figure 7:
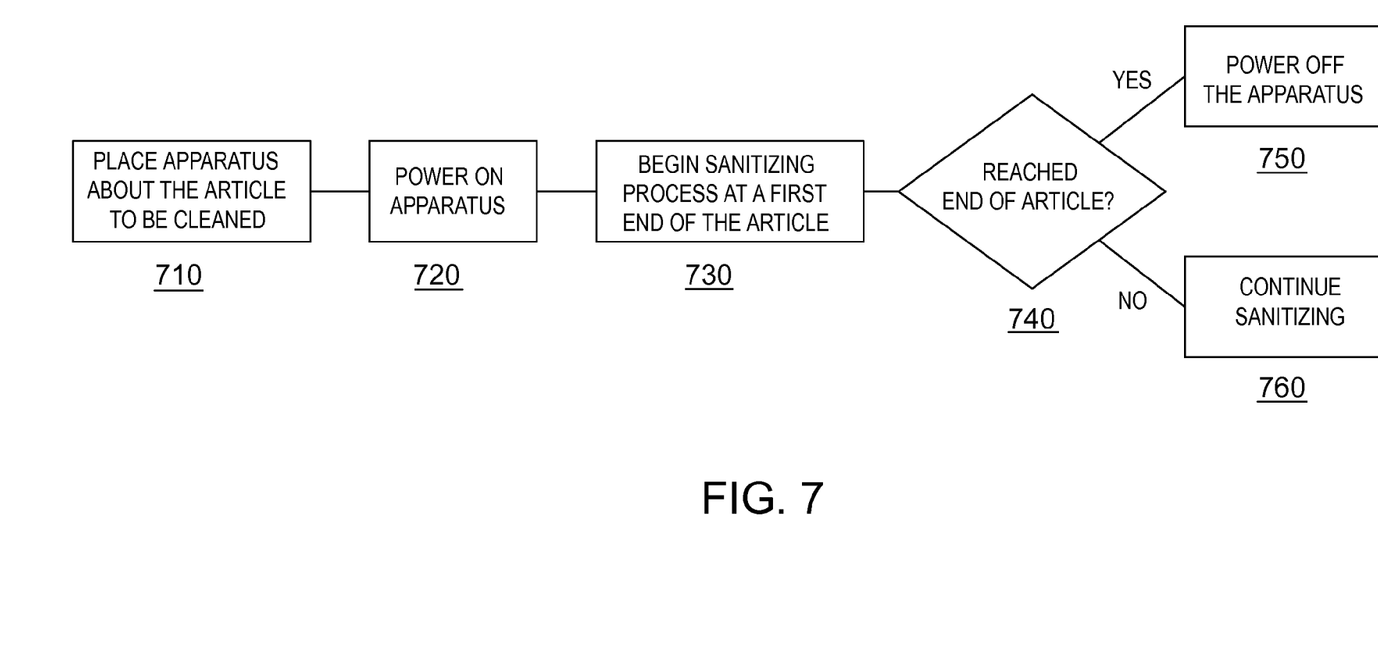
FIG. 7 is a flow chart depicting operation of the cleaning apparatus.

Operation and use of the apparatus 10 for sanitizing the article to be cleaned 1 is illustrated in the flow chart of FIG. 7. The operator places the apparatus about the article to be cleaned 710. The operator then powers on the apparatus 720. The apparatus then begins the sanitizing process at a first end of the article 730. The apparatus then determines when an end of the article has been reached 740. If the end of the article has been reached, the apparatus may shut off 750. If the end of the article has not been reached, the apparatus may continue in operation 760.

Figure 8:
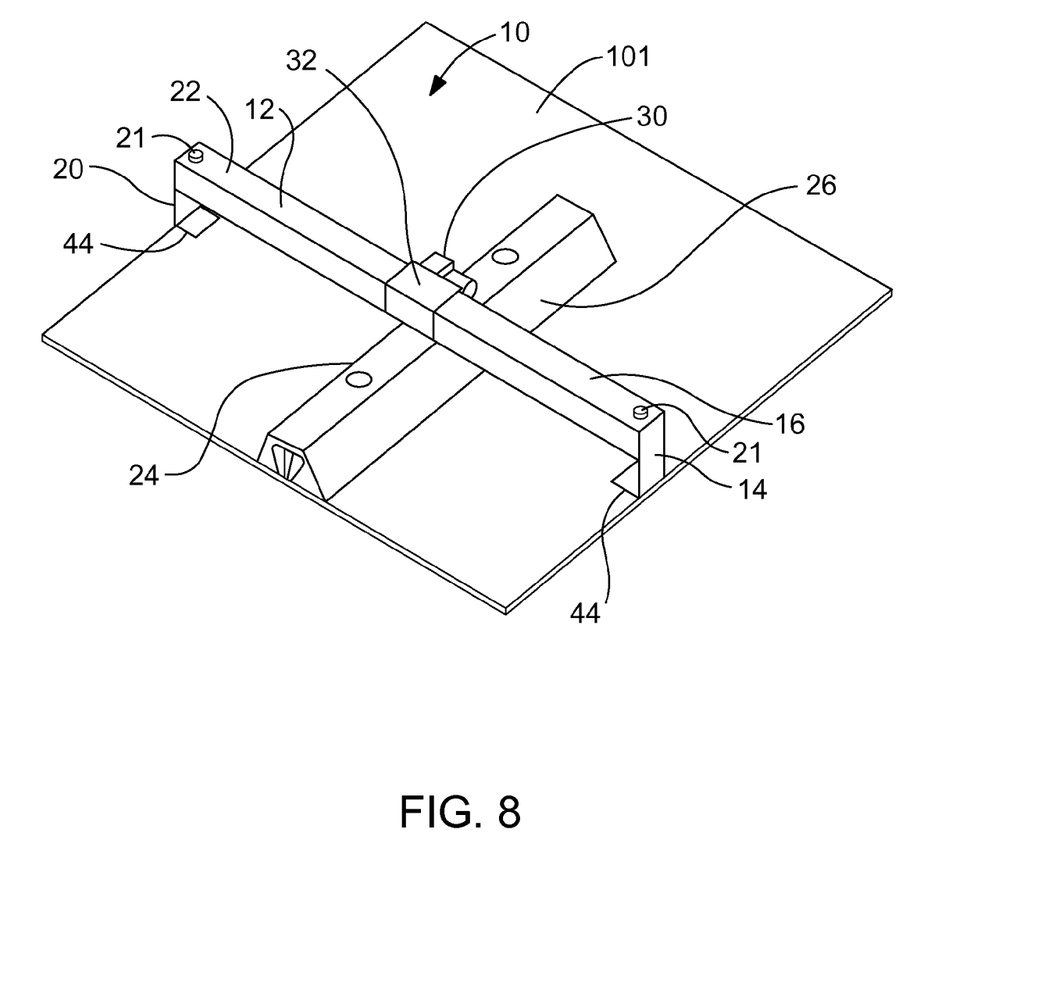
FIG. 8 is a perspective view of the cleaning apparatus installed upon an article to be cleaned.

The apparatus 10 is shown installed upon an article to be cleaned 101 according to one or more embodiments in FIG. 8. As illustrated, the article to be cleaned 101 may be a carpet or surface area rug. Operation of the apparatus 10 is similar to that which is described in regards to FIGS. 1-7. The apparatus 10 is installed on the article 101 by placing the horizontally extending members 44 on an end of each of the first engaging member 14 and the second engaging member 20 such that the horizontally extending members 44 are positioned on a lowermost portion thereof when installed on an article 101 as illustrated in FIG. 8. In one or more embodiments, a plurality of first engaging members 14 and second engaging members 20 having varying sizes may be provided for further adjustability thereof. Additionally, in one or more embodiments, the first engaging members 14 and second engaging members 20 may have a telescopic configuration for further adjustability thereof.

Figure 9:
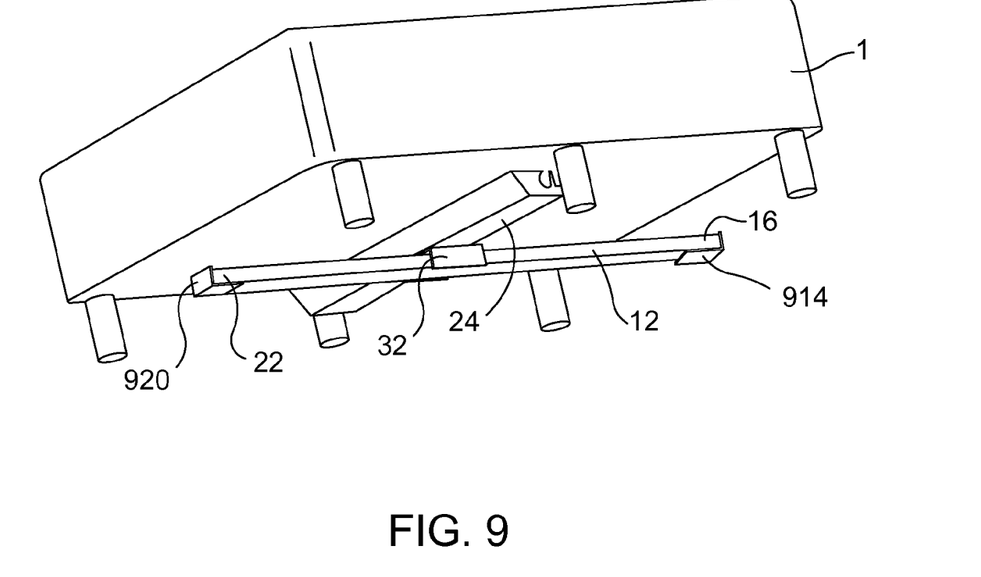
FIG. 9 is a bottom facing perspective view of the cleaning apparatus installed about an underside of the article to be cleaned in FIG. 1.

Similarly, the apparatus 10 is shown in FIG. 9 installed on an underside of the article to be cleaned 1. In this manner, the apparatus 10 may be provided for scanning the underside of an article to be cleaned 1 such as a bed as illustrated. This apparatus 10 may include a first engaging member 914 and second engaging member 920 that are configured for engaging against a floor surface and providing sufficient clearance between the mount 12 and the surrounding floor sruface to allow slideable movement of the collar 32.

Figure 10:
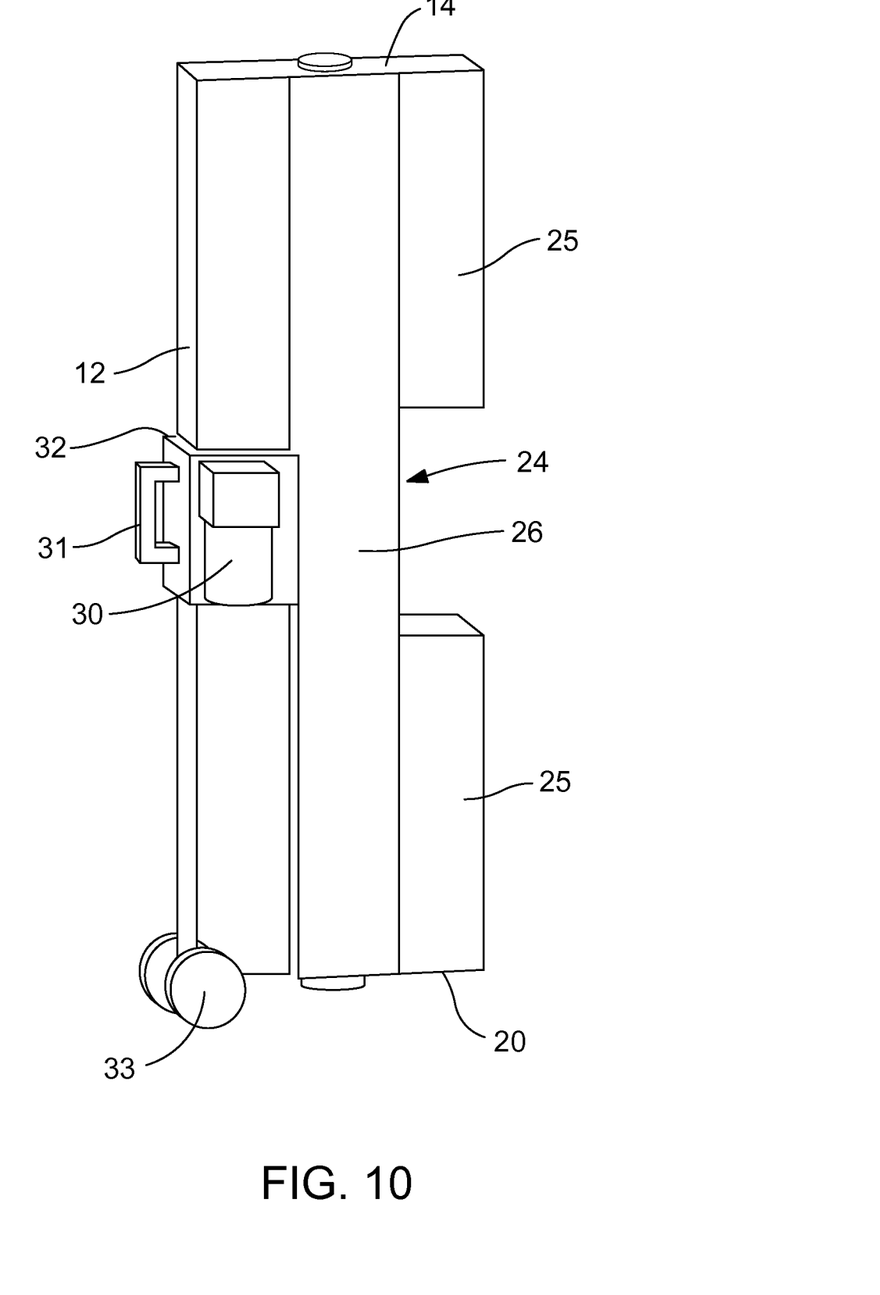
FIG. 10 is a perspective view of the cleaning apparatus in a transportable mode.

As illustrated in FIG. 10, the apparatus 10 is configured for fold-up assembly and easy storage. For example, the casing 24 may be telescopic so as to fit variously sized articles. Likewise, the mount member 12 may also be telescopic so as to fit variously sized articles. This will allow the apparatus 10 to be easily transported from each respective location. In this manner, the apparatus 10 may further include a handle 31 and rolling wheels 33 or other appropriate mechanisms for providing ease of transport.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A cleaning apparatus comprising:
   a mount member configured for extending along a dimension of an article of furnishing to be cleaned;
   a first engaging member carried on a first end of the mount member and a second engaging member carried on a second end of the mount member, the first and second engaging members cooperating for engagement with the article of furnishing to be cleaned; and
   a casing positioned in a space between the mount member and the article of furnishing to be cleaned and configured for slideable translation about the mount member in a direction extending between the first engaging member and the second engaging member along the dimension of the article of furnishing to be cleaned and defining a volume in which a sanitizing device is carried therein;
   wherein the casing and mount member are translatable therebetween such that the apparatus defines a transport orientation in which the mount member and casing are generally longitudinally aligned and a cleaning orientation in which the mount member and casing are generally longitudinally transverse to one another.

2. The apparatus according to claim 1, further including a drive motor coupled to the casing for translating the casing about the mount member.

3. The apparatus according to claim 1, wherein the casing carries a collar at a medial position thereof that is slideably received on the mount member.

4. The apparatus according to claim 1, wherein the sanitizing device comprises an ultraviolet light source for sanitizing the article to be cleaned.

5. The apparatus according to claim 1, wherein the sanitizing device comprises a vacuum for sanitizing the article to be cleaned.

6. The apparatus according to claim 1, wherein the sanitizing device includes a fluid spraying device for spraying fluids for sanitizing the article to be cleaned.

7. The apparatus according to claim 1, wherein the casing further carries a perturbator for perturbing the article to be cleaned.

8. The apparatus according to claim 1, wherein each the first and second engaging members define a horizontally extending stop member for resting upon an apparatus facing surface of the article to be cleaned, and further wherein, the horizontally extending stop members are selectively positionable about each respective first and second engaging members to thereby adjust a distance between an article facing surface of the casing and an apparatus facing surface of the article to be cleaned.

9. The apparatus according to claim 1, wherein the mount member is extendable to fit the article to be cleaned.

10. The apparatus according to claim 1, wherein the casing defines end sections that are hingedly coupled to a main section, the end sections carrying article sanitizing devices for sanitizing the article of furnishing.

11. The cleaning apparatus according to claim 1, wherein the casing extends generally perpendicularly relative to the mount member.

12. The cleaning apparatus according to claim 1, wherein the sanitizing device is a fluid sprayer.

13. A cleaning apparatus comprising:
a mount member configured for extending along a major dimension of an article of furnishing to be cleaned and maintaining a predetermined distance from an apparatus facing surface of the article of furnishing to be cleaned; and
a casing carried by the mount member in a space between the mount member and the article of furnishing to be cleaned and that is configured for slideable translation about the mount member in a direction extending between a first engaging member and a second engaging member along the major dimension of the article and that defines an article sanitizing portion on an article facing portion thereof,
wherein the article sanitizing portion includes a sanitizing device for sanitizing the article to be cleaned and an article facing surface of the casing maintaining closely-spaced apart arrangement relative to a surface of the article of furnishing that faces the cleaning apparatus, and
wherein the casing and mount member are translatable therebetween such that the apparatus defines a transport orientation in which the mount member and casing are generally longitudinally aligned and a cleaning orientation in which the mount member and casing are generally longitudinally transverse to one another.

14. The apparatus according to claim 13, further including a drive motor coupled to the casing for translating the casing about the mount member in the direction extending between the first engaging member and the second engaging member.

15. The apparatus according to claim 13, wherein the casing carries a collar that is slideably received on the mount member.

16. The apparatus according to claim 13, wherein the sanitizing device consists of an ultraviolet light source for sanitizing the article to be cleaned, a vacuum for sanitizing the article to be cleaned, a fluid dispensing device for spraying fluids for sanitizing the article to be cleaned, or a combination thereof.

17. The apparatus according to claim 13, wherein the casing further carries a perturbator for perturbing the article to be cleaned.

18. The apparatus according to claim 13, further including first and second engaging members on respective first and second ends of the mount member, the first and second engaging members cooperating for engagement about the article to be cleaned, the mount member defining a support that extends between respective ends of a longitudinal axis of the article of furnishing.

19. The apparatus according to claim 18, wherein the first and second engaging members define a horizontally extending stop member for resting upon an apparatus facing surface of the article to be cleaned.

20. The apparatus according to claim 13, wherein the mount member is extendable to fit the article to be cleaned.

21. The apparatus according to claim 13, wherein the casing defines end sections that are hingedly coupled to a main section, the end sections carrying article sanitizing devices for sanitizing the article of furnishing.

22. A cleaning apparatus comprising:
a mount member configured for extending along a major dimension of an article of furnishing to be cleaned and maintaining a predetermined distance from an apparatus facing surface of the article of furnishing to be cleaned;
a first engaging member carried on a first end of the mount member and a second engaging member carried on a second end of the mount member, the first and second engaging members cooperating for engagement about the article of furnishing to be cleaned; and
a casing carried at a medial position thereof by the mount member in a space between the mount member and the article of furnishing to be cleaned and that is configured for slideable translation about the mount member along the major dimension of the article of furnishing and that defines an article sanitizing portion on an article facing portion thereof, the article sanitizing portion being in closely-spaced arrangement relative to a surface of the article of furnishing that faces the cleaning apparatus,
wherein the article sanitizing portion includes a sanitizing device for sanitizing the article of furnishing to be cleaned,
and wherein the casing and mount member are translatable therebetween such that the apparatus defines a transport orientation in which the mount member and casing are generally longitudinally aligned and a cleaning orientation in which the mount member and casing are generally longitudinally transverse to one another.

* * * * *